United States Patent [19]

Kranz et al.

[11] 4,196,150
[45] Apr. 1, 1980

[54] 1-CHLORO-3,3-DIMETHYL-BUTAN-2-ONE

[75] Inventors: Eckart Kranz, Wuppertal; Rüdiger Schubart, Bergisch-Gladbach; Herbert Schwarz, Leverkusen; Peter Siegle, Cologne; Heinrich Steude, Leverkusen, all of Fed. Rep. of Germany

[73] Assignee: Bayer Aktiengesellschaft, Leverkusen, Fed. Rep. of Germany

[21] Appl. No.: 891,561

[22] Filed: Mar. 29, 1978

[30] Foreign Application Priority Data

Apr. 16, 1977 [DE] Fed. Rep. of Germany ....... 2716896

[51] Int. Cl.² .............................................. C07C 45/00
[52] U.S. Cl. ................................................. 260/593 H
[58] Field of Search ..................................... 260/593 H

[56] References Cited

U.S. PATENT DOCUMENTS

| | | | |
|---|---|---|---|
| 2,120,392 | 6/1938 | Calkins | 260/593 H |
| 2,168,260 | 8/1939 | Heisel et al. | 260/593 H |
| 2,235,562 | 3/1941 | Rahrs | 260/593 H |
| 2,243,484 | 5/1941 | Morey | 260/593 H |
| 3,397,240 | 8/1968 | Kaufman et al. | 260/593 H |

OTHER PUBLICATIONS

Fujira, Chem. Abst., vol. 53, #5185d, (1959).
Hill et al., J.A.C.S., vol. 55, pp. 2509–2512, (1933).

*Primary Examiner*—James H. Reamer
*Attorney, Agent, or Firm*—Sprung, Felfe, Horn, Lynch & Kramer

[57] ABSTRACT

A process for preparing monochloropinacoline (1-chloro-3,3-dimethyl-butan-2-one) by contacting a stoichiometric excess of pinacoline with chlorine at a temperature of −20° to +70° C.

7 Claims, 1 Drawing Figure

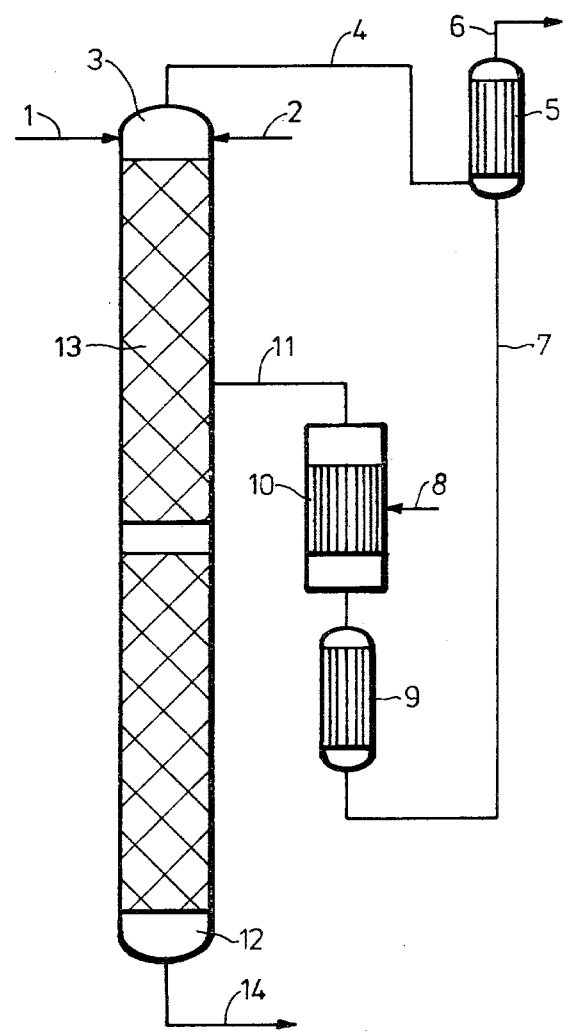

1-CHLORO-3,3-DIMETHYL-BUTAN-2-ONE

BACKGROUND OF THE INVENTION

1. Field of the Invention

The invention relates to a process for the preparation of 1-chloro-3,3-dimethyl-butan-2-one (monochloropinacoline).

2. Discussion of the Prior Art

It is known that monochloropinacoline is obtained when pinacoline is chlorinated in the presence of a solvent, such as, for example, carbon tetrachloride, chloroform or carbon disulphide, at room temperature under UV radiation (J. Am. Chem. Soc. 55, 2,509 to 2,512 (1933)). However, the yield of 23% is very low.

Similar processes which are carried out in the presence or in the absence of water or in the presence of catalysts, such as, for example, iron or iodine, or in the presence of buffer substances, such as sodium carbonate, or which are carried out electrolytically lead to no improvement in yield (J. Am. Chem. Soc. 55, 2,509 to 2,512 (1933)).

The reaction of pinacoline with equivalent amounts of chlorine to give monochloropinacoline without a solvent at 0° C. has also been disclosed (C.A. 53, 5,185 (1959)). This process has the disadvantage that the reaction is only incomplete and the yield is low. Increasing the temperature to 20 or 40° C. leads to increased formation of dichloropinacoline.

Furthermore, it has been disclosed that monochloropinacoline is obtained by gas phase chlorination of pinacoline by passing a dry stream of chlorine into the gas phase of pinacoline and separating the reaction products by fractional distillation (J. Org. Chem. 11, 781 to 787 (1946)). However, this process has the disadvantage that considerable amounts of by-products, such as 1,1-dichloro-3,3-dimethyl-butan-2-one and 1,4- dichloro-3,3-dimethyl-butan-2-one, are formed.

In addition, it has been disclosed that the chlorination of pinacoline to give monochloropinacoline can be carried out with seleniumoxy dichloride (J. Org. Chem. 28, 1,128 (1963)). The yield of the reaction is low here also.

SUMMARY OF THE INVENTION

A process has been found for the preparation of monochloropinacoline by chlorinating pinacoline, in which an excess of pinacoline, which as a temperature of −20 to 70° C., is reacted with clorine.

The process according to the invention can be illustrated with the aid of the following equation:

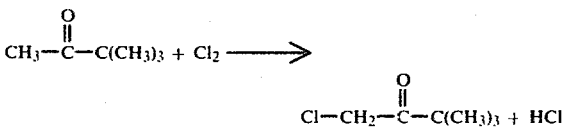

An excess of pinacoline is reacted with chlorine by the process according to the invention. For reasons of expediency, in general an excess of 1 to 50 mols, preferably of 5 to 20 mols, of pinacoline is employed per mol of chlorine.

The process according to the invention is carried out in a temperature range from −20° to 160° C., preferably from 0° to 80° C.

In the process according to the invention, the temperature of the pinacoline fed to the reaction is in the range from −20° to 70° C., preferably from −10° to 20° C.

The process according to the invention can be carried out under reduced, normal or elevated pressure, preferably under normal pressure.

Anhydrous pinacoline can be used for the process according to the invention. Anhydrous pinacoline can be obtained, for example, by subjecting industrial pinacoline to incipient distillation.

In a preferred embodiment of the process according to the invention, the reaction is carried out with water-containing pinacoline. In general, it is possible to use pinacoline which contains up to 20 percent by weight, preferably from 0.01 to 5 percent by weight, of water.

In a further preferred embodiment of the process according to the invention, the reaction is carried out with the exclusion of light.

In the process according to the invention, gaseous chlorine is passed into the reaction chamber. The chlorine can be used without further diluents. However, it is also possible to dilute the gaseous chlorine with inert gases, such as nitrogen or argon. The proportion of diluent can then be up to 90%, preferably from 30 to 50%, of the gas employed.

The process according to the invention is preferably carried out in a reaction apparatus in which the pinacoline has a short residence time and is chlorinated to the extent of only a few percent by weight and the chlorination mixture formed is removed from the reaction apparatus immediately after the chlorination and further chlorination of the already chlorinated reaction mixture is thus avoided.

It is possible to carry out the process according to the invention either discontinuously or continuously.

BRIEF DESCRIPTION OF DRAWING

Referring to the accompanying drawing, there is shown therein a schematic flow diagram showing how the process of the invention can be carried our.

DESCRIPTION OF SPECIFIC EMBODIMENT

An embodiment of the process according to the invention may be illustrated with the aid of the drawing:

The pinacoline is fed via (1) and, if appropriate, the water is fed via (2) into the head (3) of a column (13) which has an inlet (11) in the middle section and an outlet (14) in the bottom (12) and which is packed or provided with glass trays. The pinacoline and, if appropriate, the water, evaporate in the head (3) of the column and are passed via feed line (4) to the dephlegmator (5) and condensed there. The condensed, optionally water-containing pinacoline is passed via feed line (7) to the cooler (9), in which the liquid pinacoline is brought to the temperature at which it is passed into the reactor (10). Gaseous chlorine is fed via feed line (8) into the reactor (10), which can be appropriately warmed or cooled to the desired reaction temperature. It is possible to darken the reactor (10). The reactor, for example a Venturi tube, is designed so that the reaction product can be led out of the reactor as rapidly as possible after the reaction.

The reaction mixture formed, which essentially contains monochloropinacoline, unreacted pinacoline and hydrogen chloride, is passed through the inlet (11) into the middle section of the column (13). The reaction mixture formed is separated in the column (13). The unreacted pinacoline and the hydrogen chloride are removed via the head (3) of the column (13); both compounds are passed via feed line (4) into the dephlegmator (5), in which the hydrogen chloride is separated off via head (6), whilst the pinacoline is fed again to the reaction circulation.

The monochloropinacoline formed during the reaction is removed at the bottom (12) of the column (13) via the outlet (14).

It is advantageously possible to prepare monochloropinacoline in high yields on an industrial scale with the aid of the process according to the invention. Virtually no by-products are formed in the process according to the invention. By circulating the pinacoline, virtually no loss of pinacoline employed occurs.

It is surprising that monochloropinacoline is formed in high yield and purity under the process conditions according to the invention since, with regard to the state of the art, it should have been expected that unsatisfactory amounts of monochloropinacoline and large amounts of by-products, such as 1,1-dichloropinacoline, 1,4-dichloropinacoline and 4-chloropinacoline, are formed in the chlorination of pinacoline in the liquid phase and without a solvent. Monochlorinalcoline can be reacted first with substituted phenols, e.g. 4-chlorophenol, and subsequently with sulfuryl chloride to yield e.g.

1-(4'-chlorophenoxy)-1-chloro-3,3-dimethyl-butan--2-one (DT-OS(German Published Specification) No. 2,401,715). The obtained substances yield on subsequent reaction with triazoles or imidazoles products of known fungicidal and antimicrobial activity, e.g. 1-(4'-chlorophenoxy)-3,3-dimethyl-1-(1,2,4-triazol-1-yl)-butan-2-one (DT-OS (German Published Specification) No. 2,201,063 and 2,401,715) and 1-(4'-chlorophenoxy)-3,3-dimethyl-1- (imidazol-1-yl)-butan-2-one (DT-OS (German Published Specification) No. 2,105,490).

In the example which follows, monochloropinacoline is prepared in a reaction apparatus such as is represented in the drawing.

EXAMPLE 350 ml of pinacoline per hour, with a water content of 0.1% by weight, are passed into the head (3) of the column of a glass tray column (13) (13 trays, 50 mm cross section). The water-containing pinacoline evaporates and is condensed in the dephlegmator (5), which is cooled with water, and passed via feed line (7) to the cooler (9), in which it is cooled to $-10°$ C. The pinacoline is passed from the cooler (9) to the reactor (10), in which it is reacted, at a flow rate of 1 m/second, with the chlorine fed in via (8). The reaction product is introduced at the 10th tray of the column (13) and then separated. Unreacted pinacoline and the hydrogen chloride formed are removed via the head of the column (13). The pinacoline is condensed in the dephlegmator (5) and is recycled to the reaction. 350 ml/hour of monochloropinacoline (with a monochloropinacoline content of 92.5%) are removed at the bottom of the column (13). Boiling point=170° to 175° C.

What is claimed is:

1. A process for preparing monochloropinacoline which comprises contacting a stoichiometric excess of pinacoline with chlorine at a temperature of $-20°$ to $+70°$ C. employing between 1 and 50 mols excess of pinacoline per mol of chlorine.
2. A process according to claim 1 wherein the reaction is carried out in the presence of water.
3. A process according to claim 1 carried out in the presence of up to 20% by weight water.
4. A process according to claim 1 wherein the reaction is carried out with the exclusion of light.
5. A process according to claim 1 wherein the reaction is carried out in the absence of an organic solvent.
6. A process according to claim 1 wherein said pinacoline is liquid pinacoline.
7. A process according to claim 1 wherein pinacoline is passed into the head of a column, evaporated and removed from said column, condensed and condensed pinacoline is introduced into a reactor into which is introduced said chlorine and monochloropinacoline is removed from the bottom of said column.

* * * * *